United States Patent [19]

Takamiya et al.

[11] Patent Number: 4,832,005
[45] Date of Patent: * May 23, 1989

[54] MEDICAL APPLIANCE DRIVING APPARATUS

[75] Inventors: Sanshiro Takamiya, Nagoya; Masakazu Nakagawa, Tokyo, both of Japan

[73] Assignee: Aisin Seiki Kabushiki Kaisha, Aichi, Japan

[*] Notice: The portion of the term of this patent subsequent to Jan. 3, 2006 has been disclaimed.

[21] Appl. No.: 30,751

[22] Filed: Mar. 26, 1987

[30] Foreign Application Priority Data

Mar. 26, 1986 [JP] Japan .................... 61-068009

[51] Int. Cl.⁴ .................................. A61M 25/00
[52] U.S. Cl. ...................................... 600/18
[58] Field of Search ............. 604/99; 128/1 D, 752

[56] References Cited

U.S. PATENT DOCUMENTS

| | | | |
|---|---|---|---|
| 3,452,738 | 7/1969 | Jones | 128/1 D |
| 3,465,746 | 9/1969 | Guarino | 128/1 D |
| 3,698,381 | 10/1972 | Federico et al. | 128/1 D |
| 4,162,543 | 7/1979 | Shumakov et al. | 128/1 D X |
| 4,323,071 | 4/1982 | Simpson et al. | 604/99 X |
| 4,332,254 | 6/1982 | Lundquist | 604/99 X |
| 4,361,152 | 11/1982 | Patel | 604/99 |
| 4,439,186 | 3/1984 | Kuhl | 604/99 |
| 4,546,760 | 10/1985 | Zuzuki et al. | 128/1 D |
| 4,548,550 | 10/1985 | Tsuji | 417/390 |
| 4,556,997 | 12/1985 | Takamiya et al. | 623/3 |
| 4,573,883 | 3/1986 | Noon et al. | 604/99 |
| 4,583,525 | 4/1986 | Suzuki et al. | 128/1 D |
| 4,648,385 | 3/1987 | Oumi et al. | 128/1 D |
| 4,653,539 | 3/1987 | Bell | 604/99 X |
| 4,654,027 | 3/1987 | Drajan et al. | 604/99 |

Primary Examiner—Edward M. Coven
Attorney, Agent, or Firm—Sughrue, Mion, Zinn, Macpeak & Seas

[57] ABSTRACT

A medical appliance driving apparatus has a switching valve connected to both positive and negative pressure sources to output positive and negative pressures while switching them from one to the other, and an isolator having an input chamber and an output chamber which are defined by a movable membrane, the input chamber being connected to the switching valve. A solenoid valve is connected to the output chamber of the isolator, and a microcomputer is provided for switching the switching valve to the positive pressure side or the negative pressure side and controlling the operation of the solenoid valve. When the switching valve is activated to the positive pressure source side and the solenoid valve is opened, a positive pressure which is supplied to the input chamber causes the movable membrane to move in a direction in which the medical appliance is expanded. Thereafter, the solenoid valve is closed to maintain the pressure supplied to the medical appliance as it is, and the switching valve is switched to the negative pressure source side to supply a negative pressure to the input chamber of the isolator. Accordingly, the input side of the isolator can be communicated with the negative pressure source while the medical appliance is maintained in the expanded state. Thus, it is possible to quickly switch the state of the medical appliance from expansion to contraction.

12 Claims, 4 Drawing Sheets

MEDICAL APPLIANCE DRIVING APPARATUS

BACKGROUND OF THE INVENTION

1. Field of the Invention

The present invention relates to a medical appliance driving apparatus designed to expand and contract a medical appliance such as an artifial heart pump or an intraaorta balloon pump by alternately supplying positive and negative pressures thereto. More particularly, the present invention pertains to an apparatus for driving an intraaorta balloon pump.

2. Description of the Related Art

Medical appliance driving apparatus are demanded to increase the speed of expansion and contraction of the associated medical appliances. It is preferable, in order to meet such requirements, to make steep the rise (or fall) of the pressure supplied to the medical appliances. For this reason, one type of driving apparatus employs an accumulator to prevent variations in pressure. However, it is necessary to considerably increase the capacity of the accumulator in order to absorb a rise or lowering in pressure produced in the accumulator when the state of the medical appliance is changed from expansion to contraction or vice versa. Accordingly, it is difficult to reduce the overall size of the driving apparatus.

There is another type of medical appliance driving apparatus wherein a solenoid valve is disposed in parallel to a pressure regulating valve and a pressure from a pressure source such as a compressor or a vacuum pump is directly supplied to the medical appliance by controlling the solenoid valve so as to be opened and closed at a predetermined timing, thereby making compensation for the rise of pressure supplied to the medical appliance.

For example, a driving apparatus disclosed in Japanese Patent Laid-Open No. 177062/1984 is arranged such that, while a negative pressure is being supplied to a medical appliance, a positive pressure is directly led from a compressor through a solenoid valve and kept higher than a set pressure regulated by a pressure regulating valve to thereby compensate for the rise of pressure when a positive pressure is supplied to the medical appliance.

Driving apparatus disclosed in Japanese Patent Laid-Open Nos. 206698/1984 and 207158/1984, respectively, are arranged such that, when a positive pressure is supplied to a medical appliance, a positive pressure from a compressor is directly supplied through a solenoid valve for a predetermined period of time to thereby compensate for the rise of pressure supplied to the medical appliance.

Driving apparatus disclosed in Japanese Patent Laid-Open Nos. 206699/1984 and 207158/1984 are provided with an auxiliary accumulator for accumulating a positive pressure from a compressor in addition to an accumulator for accumulating a regulated pressure, and when the regulated pressure is supplied to the medical appliance, the pressure accumulated in the auxiliary accumulator is supplied together with said regulated pressure to thereby make compensation for the rise of pressure supplied to the medical appliance.

A driving apparatus disclosed in Japanese Patent Laid-Open No. 106462/1985 is arranged such that, when a positive pressure is supplied to a medical appliance, a positive pressure from a compressor is directly supplied through a solenoid valve to thereby compensate for the rise of pressure supplied to the medical appliance, and when the pressure in the medical appliance reaches a predetermined value, the solenoid valve is closed.

In all of these driving apparatus, a pressure from a pressure source is directly led to a medical appliance in order to compensate for the rise of pressure supplied to the medical appliance. Accordingly, when the medical appliance is to be expanded, a positive pressure fluid is needed to compensate for a negative pressure in the pipe line or the like, whereas, when the medical appliance is to be contracted, a negative pressure fluid is needed to compensate for a positive pressure in the pipe line. For this reason, it has heretofore been unavoidable that the rise of pressure at the time of switching the state of the medical appliance from expansion to contraction and vice versa is somewhat slow.

SUMMARY OF THE INVENTION

In view of the above-described circumstances, it is a primary object of the present invention to provide a medical appliance driving apparatus which is so designed that said rise of pressure is as steep as possible.

To this end, the present invention provides a medical appliance driving apparatus comprising: switching valve means connected to both positive and negative pressure sources to output positive and negative pressures while switching them from one to the other; isolator means having an input chamber and an output chamber which are defined by a movable membrane, the input chamber being connected to the switching valve means; valve means connected to the output chamber of the isolator means; and electronic control means for switching said switching valve means to the positive pressure side or the negative pressure side and for controlling the operation of the valve means. By virtue of this arrangement, when the switching valve means is activated to the positive pressure source side and the valve means is opened, a positive pressure which is supplied to the input chamber causes the movable membrane to move in a direction in which the medical appliance is expanded. Thereafter, the valve means is closed to maintain the pressure supplied to the medical appliance as it is, and the switching valve means is switched to the negative pressure source side to supply a negative pressure to the input chamber of the isolator means.

Accordingly, the input side of the isolator means can be communicated with the negative pressure source while the medical appliance is maintained in the expanded state. Therefore, when a negative pressure is supplied to the medical appliance during the subsequent contraction period by opening the valve means, the input chamber of the isolator means has already been supplied with the required negative pressure. Thus, it is possible to quickly switch the state of the medical appliance from expansion to contraction.

According to another aspect of the present invention, there is provided a medical appliance driving apparatus comprising: switching valve means connected to both positive and negative pressure sources to output both positive and negative pressures; isolator means having an input chamber and an output chamber which are defined by a movable membrane, the input chamber being connected to the switching valve means; valve means connected to the output chamber of the isolator means; position detecting means for detecting the position of the movable membrane of the isolator means;

and electronic control means which closes the valve means when the movable membrane has moved to a predetermined position in a state wherein the switching valve means is activated to the positive pressure source side and the valve means is in its open position, and which further activates the switching valve means to the negative pressure source side.

According to this arrangement, when the switching valve means is activated to the positive pressure source side and the valve means is opened, a positive pressure supplied to the input chamber causes the movable membrane to move in a direction in which the medical appliance is expanded. When the movable membrane reaches a predetermined position, the valve means is closed to maintain the pressure in the medical appliance at a constant level. Then, the switching valve means is switched to the negative pressure source side. In other words, the state of the medical appliance is judged on the basis of the position of the movable membrane.

Further, according to the present invention, when the movable membrane is moved to reach a second predetermined position in a state wherein the switching valve means is activated to the negative pressure source side and the valve means is in its open position, the valve means is closed, and the switching valve means is activated to the positive pressure source side.

Thus, when the switching valve means is activated to the negative pressure source side and the valve means is opened, a negative pressure supplied to the input chamber causes the movable membrane to move in a direction in which the medical appliance is contracted. When the movable membrane reaches the second predetermined position, the valve means is closed to maintain the pressure inside the medical appliance at a constant level. In this state, the switching valve means is switched to the positive pressure source side. Accordingly, the input chamber of the isolator means can be communicated with the positive pressure source while the medical appliance is maintained in the contracted state. Therefore, when a positive pressure is supplied to the medical appliance during the subsequent expansion period by opening the valve means, the input chamber of the isolator means has already been supplied with the required positive pressure. Accordingly, it is possible to quickly switch the state of the medical appliance from contraction to expansion.

The above and other objects, features and advantages of the present invention will become clear from the following description of the preferred embodiment thereof taken in conjunction with the accompanying drawings.

DESCRIPTION OF THE PREFERRED EMBODIMENT

One embodiment of the present invention will be described hereinunder in detail with reference to the accompanying drawings.

Figure 1:
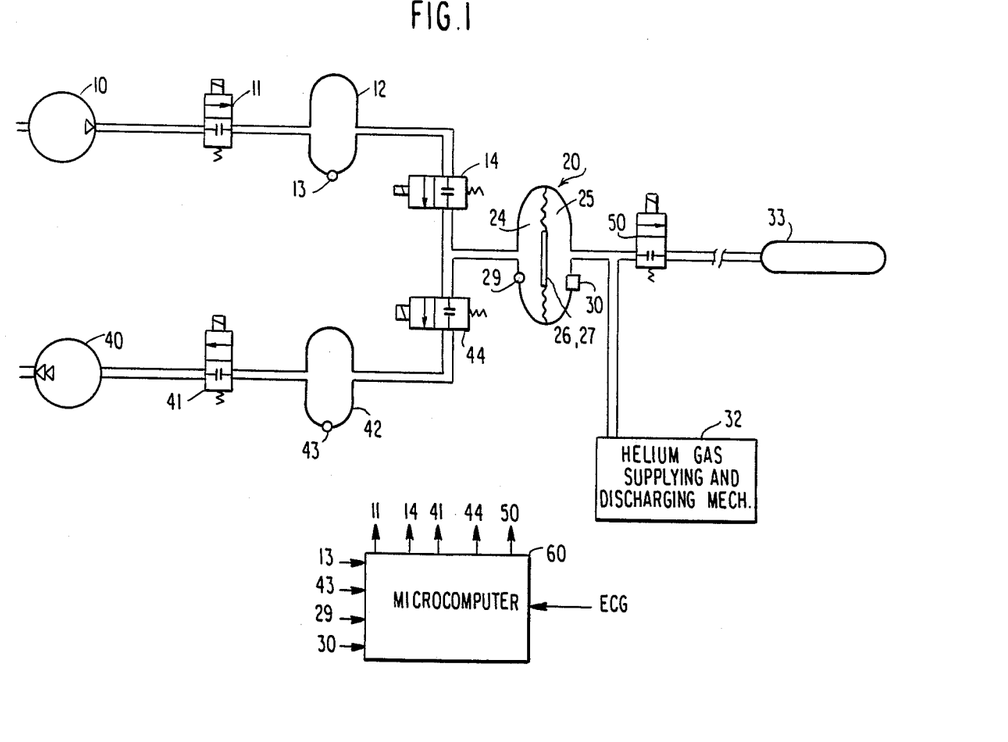
FIG. 1 is a block diagram of one embodiment of the medical appliance driving apparatus according to the present invention.

Referring first to FIG. 1, which is a block diagram of a medical appliance driving apparatus according to the present invention, the output side of a compressor 10 which serves as a positive pressure source is connected to a pressure regulating valve 11 the output side of which is, in turn, connected to a tank 12. A pressure sensor 13 for detecting pressure is disposed on the tank 12.

The output side of the tank 12 is connected to a solenoid valve 14 which serves as switching valve means. The output side of the solenoid valve 14 is connected to an isolator 20 which serves as isolator means. The isolator 20 changes a medium for driving a medical appliance from air to a gas such as helium. Thus, a driving medium is made safe for living organisms.

Figure 2:
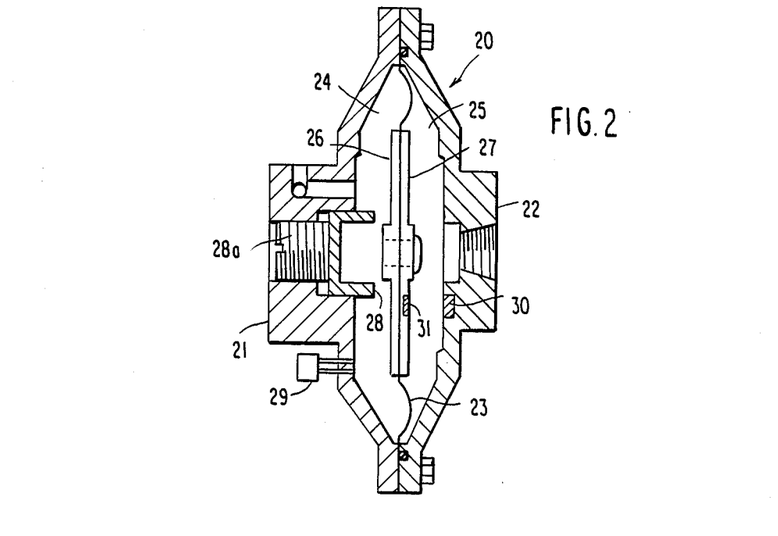
FIG. 2 is a sectional view of the isolator means shown in FIG. 1.

Referring next to FIG. 2, which shows the isolator 20 in detail, the interior of the isolator 20 is divided into an input chamber 24 and an output chamber 25 by means of a diaphragm 23 which is clamped between housings 21 and 22. Plates 26 and 27 are secured to both sides, respectively, of the central portion of the diaphragm 23. The diaphragm 23 and the plates 26, 27 define in combination a movable membrane. A limiting member 28 for limiting the amount of movement of the plate 26 is secured to the central portion of the housing 21. The limiting member 28 is in thread engagement with the housing 21 by means of a screw 28a. When turned, the limiting member 28 is moved sideways as viewed in the figure. When the limiting member 28 is moved leftward, the range within which the plates 26 and 27 can move is enlarged, whereas, when the limiting member 28 is moved rightward, said movable range is decreased.

A pressure sensor 29 which serves as pressure detecting means is disposed on the side of the housing 21 which is closer to the input chamber 24. A Hall element sensor 30 which serves as position detecting means for detecting the position of the plates 26 and 27 is disposed on the side of the housing 22 which is closer to the output chamber 25. A magnet 31 is disposed on the plate 27 so that the magnet 31 faces the Hall element sensor 30. Since the Hall element sensor 30 is capable of obtaining an output proportional to the magnitude of an external magnetic field, it is possible to detect the position of the plate 27 on the basis of the output of the sensor 30.

Referring back to FIG. 1, the output chamber 25 of the isolator 20 is connected to a helium gas supplying and discharging mechanism 32 and a solenoid valve 50 which serves as valve means. The output side of the solenoid valve 50 is connected to an intraaorta balloon pump 33 which defines a medical appliance in this embodiment. The helium gas supplying and discharging mechanism 32 serves to maintain the pressure of helium gas within the isolator 20 and the balloon pump 33 at a constant level.

The output of a vacuum pump 40 which serves as a negative pressure source is connected to a pressure regulating valve 41 the output side of which is, in turn, connected to a tank 42. A pressure sensor 43 for detecting pressure is disposed on the tank 42.

The output side of the tank 42 is connected to a solenoid valve 44 which serves as switching valve means. The output side of the solenoid valve 44 is connected to the input chamber 24 of the isolator 20.

To the input side of a microcomputer 60 which serves as electronic control means are connected the pressure sensors 13, 43 and 29 and the Hall element sensor 30, whereas, to the output side of the microcomputer 60 are connected the pressure regulating valves 11, 41 and the solenoid valves 14, 44 and 50.

The operation of the microcomputer 60 will next be explained with reference to flow charts shown in FIGS. 3, 4, 5 and 6.

Figure 3:
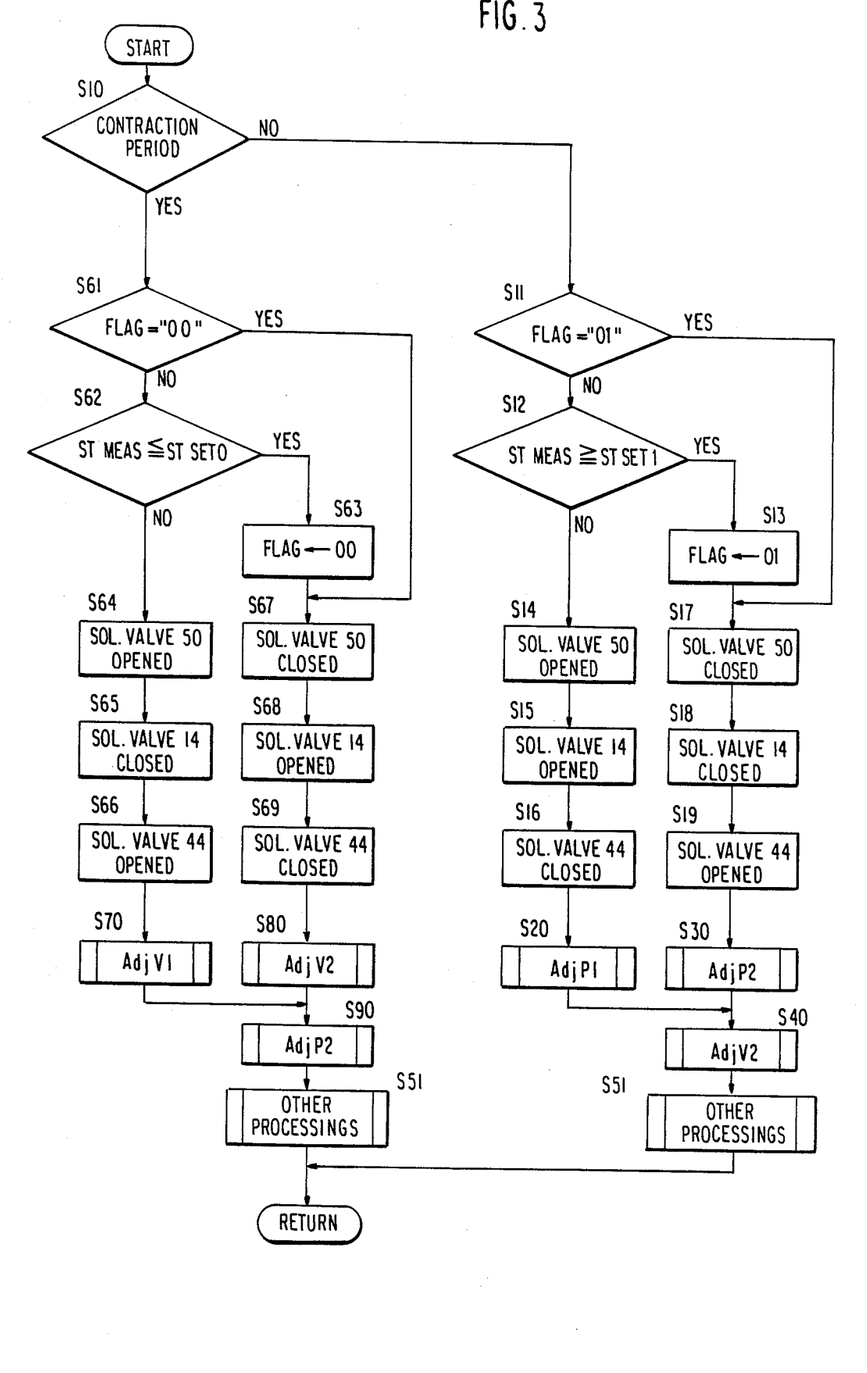
FIGS. 3, 4, 5, 6 and 7 are flow charts showing the operation of the embodiment.
Figure 4:
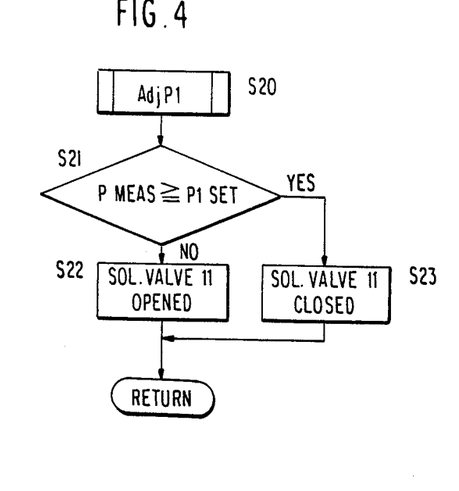
Figure 5:
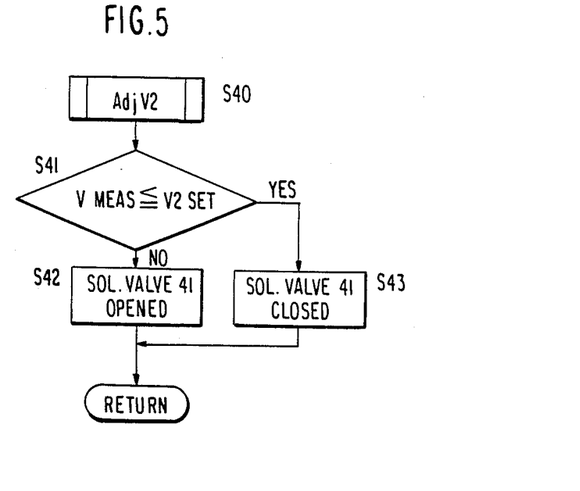
Figure 6:
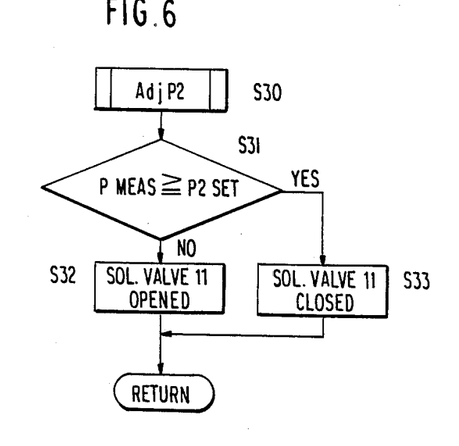

FIG. 3 shows control which is executed according to the main routine. A judgement is made in Step S10 as to whether or not the balloon pump 33 is during the contraction period. The contraction period of the balloon pump 33 is determined as follows. For example, the microcomputer 60 is externally supplied with an electrocardiogram (ECG) signal and/or a blood pressure signal concerning a living organism under treatment to perform calculation in order to obtain contraction and expansion timing which is appropriate to a particular condition of the living organism on the basis of the input data. Description of the calculation and the like is omitted herein.

When the balloon pump 33 is judged to be during the expansion period in Step S10, positive pressure supply control which is shown in infra Step S11 is executed. In this control, a judgement is first made in Step S11 as to whether or not a movable membrane position flag "01" is up. This flag "01" is set in Step S13 when it is judged in Step S12 that the position STmeas of the plate 27 detected by the Hall element sensor 30 reaches a given set position STset1 during the expansion period. Since, in this state, the flag "01" is not up, the process proceeds to Step S14, in which the solenoid valve 50 is opened to allow the output chamber 25 to communicate with the balloon pump 33. At this time, the input chamber 24 of the isolator 20 has already been communicated with the tank 12 by opening the solenoid valve 14 and closing the solenoid valve 44 as described later. In other words, the input chamber 24 is being supplied with a positive pressure and thus pressurized. Accordingly, when the solenoid valve 50 is opened, the plate 27 is immediately moved in a direction in which the balloon pump 33 is expanded, thereby starting expansion of the pump 33. It should be noted that Steps S15 and S16 are executed in order to maintain the solenoid valves 14 and 44 in the open and closed positions, respectively.

At this time, positive pressure adjusting control AdjP1 shown in Step S20 is effected. This control is shown in the flow chart of FIG. 4. A judgement is made in Step S21 as to whether or not the tank pressure Pmeas represented by a value detected by the pressure sensor 13 disposed on the tank 12 is equal to or greater than a set positive pressure value P1set. When the pressure Pmeas is less than the set value P1set, the process proceeds to Step S22, in which the pressure regulating valve 11 is opened to introduce the pressure from the compressor 10 into the tank 12. When the pressure Pmeas reaches the set value P1set, the pressure regulating valve 11 is closed in Step S23.

Referring back to FIG. 3, negative pressure adjusting control AdjV2 is carried out in Step S40. This control is executed in order to set a negative pressure required during the subsequent contraction period in the tank 42 while the balloon pump 33 is being expanded by means of the positive pressure. The negative pressure adjusting control AdjV2 will be explained below with reference to the flow chart shown in FIG. 5. A judgement is made in Step S41 as to whether or not the tank pressure Vmeas represented by a value detected by the pressure sensor 43 disposed on the tank 42 is equal to or less than a set negative pressure value V2set. When the pressure Vmeas is greter than the set value V2set, the pressure regulating valve 41 is opened in Step S42 to introduce the pressure from the vacuum pump 40 into the tank 42. When the pressure Vmeas reaches the set value V2set, the pressure regulating valve 41 is closed.

Referring back to FIG. 3, other processings are executed in Step S50, and the process returns.

When it is judged in Step S12 that the position STmeas of the plate 27 has reached the set position STset1 during the expansion period, the process proceeds to Step S13, in which the flag "01" is set, and the process then proceeds to Step S17, in which the solenoid valve 50 is closed to cut off the supply of positive pressure thereafter. Thus, the pressure in the balloon pump 33 is maintained as it is, so that the pump 33 is held in the expanded state.

The solenoid valve 14 is closed in Step S18 to cut off the supply of positive pressure into the input chamber 24. The solenoid valve 44 is opened in Step S19 to supply a negative pressure into the input chamber 24. This step is executed in order to supply a negative pressure into the input chamber 24 for the subsequent contraction period while the balloon pump 33 is maintained in the expanded state. Accordingly, while the balloon pump 33 is held in the expanded state, the input chamber 24 is pressurized so as to be held in a negative pressure state.

It should be noted that, after these processings, the pressure inside the tank 12 is set to a set value P2set for the subsequent expansion period in Step S30. This control is effected in order to set a positive pressure required during the subsequent expansion period in the tank 12 while the balloon pump 33 is held in the expanded state. This control process will be explained below with reference to the flow chart shown in FIG. 6. A judgement is made in Step S31 as to whether or not the tank pressure Pmeas represented by a value detected by the pressure sensor 13 disposed on the tank 12 is equal to or greater than a set positive pressure value P2set. When the pressure Pmeas is less than the set value P2set, the pressure regulating valve 11 is opened in Step S32 to introduce the pressure from the compressor 10 into the tank 12. When the pressure Pmeas reaches the set value P2set, the pressure regulating valve 11 is closed in Step S33.

Further, the negative pressure in the tank 42 is set to a given set negative pressure value V2set in Step S40.

The control executed during the contraction period will next be explained with reference to FIG. 3.

When it is judged in Step S10 that the balloon pump 33 is during the contraction period, negative pressure supply control shown in infra Step S61 is executed. In this control, a judgement is first made in Step S61 as to whether or not a movable membrane position flag "00" is up. This flag "00" is set in Step S63 when it is judged in Step S62 that the position STmeas of the plate 27 which is detected by the Hall element sensor 30 reaches a given set position STset0 during the contraction period. Since, in this state, the flag "00" is not up, the process proceeds to Step S64, in which the solenoid valve 50 is opened to allow the output chamber 25 to communicate with the balloon pump 33. At this time, the input chamber 24 of the isolator 20 has already been communicated with the tank 42 by opening the solenoid valve 44 and closing the solenoid valve 14 as described above.

In other words, the input chamber 24 is being supplied with a negative pressure and thus pressurized. Accordingly, when the solenoid valve 50 is opened, the plate 27 is immediately moved in a direction in which the balloon pump 33 is contracted, thereby starting contraction of the pump 33. It should be noted that Steps S65 and S66 are executed in order to maintain the solenoid valves 14 and 44 in the closed and open positions, respectively.

Figure 7:
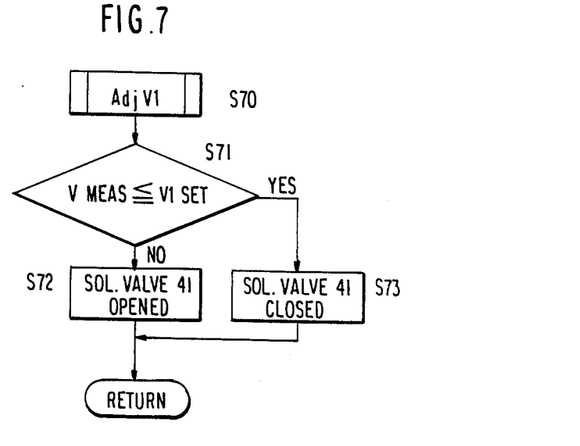

At this time, negative pressure adjusting control AdjV1 shown in Step S70 is effected. This control is shown in the flow chart of FIG. 7. A judgement is made in Step S71 as to whether or not the tank pressure Vmeas represented by a value detected by the pressure sensor 43 disposed on the tank 42 is equal to or less than a set negative pressure value V1set. When the pressure Vmeas is greater than the set value V1set, the process proceeds to Step S72, in which the pressure regulating valve 41 is opened to introduce the pressure from the vacuum pump 40 into the tank 42. When the pressure Vmeas reaches the set value V1set, the pressure regulating valve 41 is closed in Step S73.

Referring back to FIG. 3, the pressure in the tank 12 is set to the set value P2set for the subsequent expansion period in Step S90. This control is executed in order to set a positive pressure required during the subsequent expansion period in the tank 12 while the balloon pump 33 is being contracted. Since this is the same as the positive pressure adjusting control AdjP2 shown in FIG. 6, description thereof is omitted.

Referring back to FIG. 3, other processings are executed in Step S51, and the process returns.

When it is judged in Step S62 that the position STmeas of the plate 27 has reached the set position STset0 during the contraction period, the process proceeds to Step S63, in which the flag "00" is set, and the process then proceeds to Step S67, in which the solenoid valve 50 is closed to cut off the supply of negative pressure thereafter. Thus, the pressure in the balloon pump 33 is maintained as it is, so that the pump 33 is held in the contracted state.

The solenoid valve 14 is opened in Step S68 to supply a positive pressure into the input chamber 24. The solenoid valve 44 is closed in Step S69 to cut off the supply of negative pressure into the input chamber 24. This step is executed in order to supply a positive pressure into the input chamber 24 for the subsequent expansion period while the balloon pump 33 is maintained in the contracted state. Accordingly, while the balloon pump 33 is held in the contracted state, the input chamber 24 is pressurized so as to be held in a positive pressure state.

It should be noted that, after these processings, negative pressure adjusting control AdjV2 is carried out. This control is effected in order to set a negative pressure required during the subsequent contraction period in the tank 42 while the balloon pump 33 is held in the contracted state by means of the negative pressure. Since this control is the same as that explained with reference to the flow chart shown in FIG. 5, description thereof is omitted.

Figure 8:
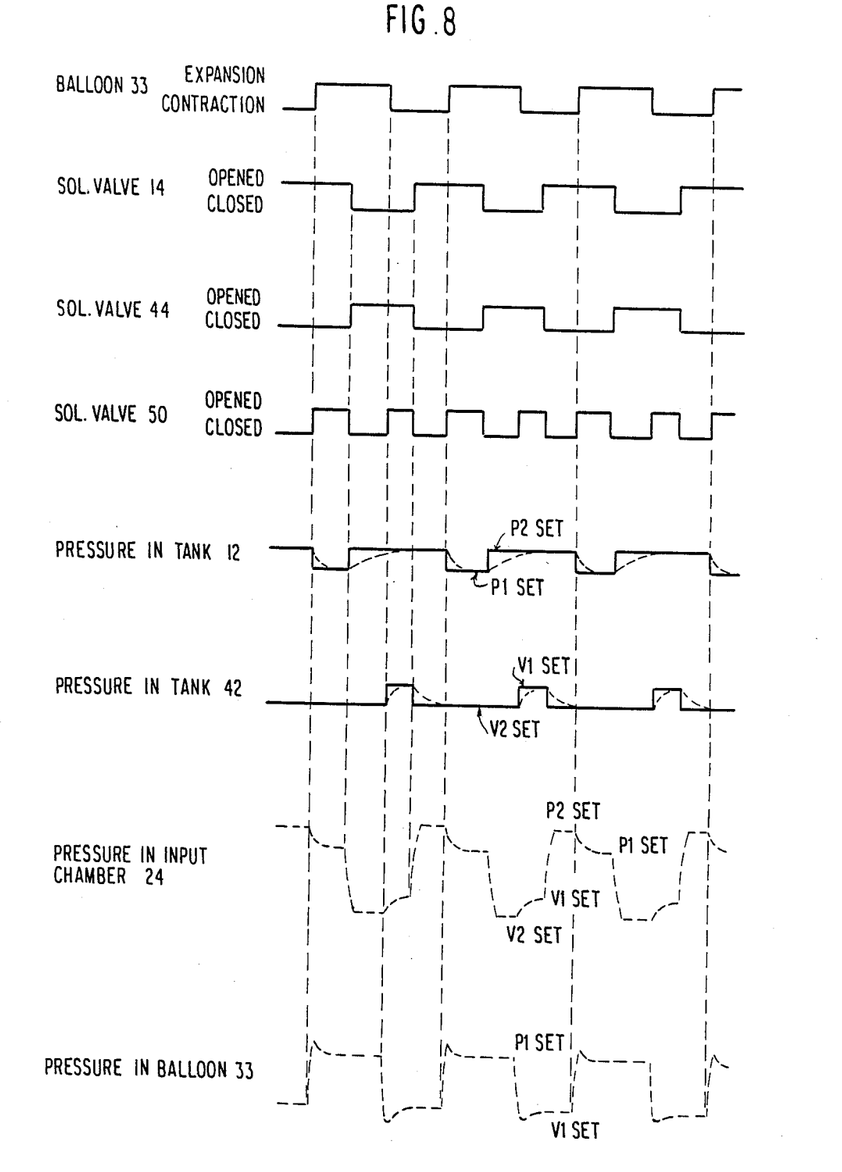
FIG. 8 is a timing chart showing the operation of the embodiment.

FIG. 8 is a chart showing the timing at which each of the solenoid valves is opened or closed. The operation of this embodiment will be summed up below with reference to this timing chart.

(i) Expansion period of the balloon pump 33:

1. Before the expansion period begins, the solenoid valve 50 is closed and the balloon pump 33 is therefore held in the contracted state. At this time, the solenoid valves 14 and 44 are in the open and closed positions, respectively. Accordingly, the pressure in the input chamber 24 is set at the set positive pressure value P2set (e.g., 300 mmHg) for the internal pressure of the positive pressure tank 12, the value P2set being set by means of the solenoid valve 11. When, in this state, the solenoid valve 50 is opened, the plate 27 is moved in a direction in which the balloon pump 33 is expanded. At this time, in order to prevent application of an excessively high pressure to the inside of the balloon pump 33, the internal pressure of the positive pressure tank 12 is adjusted so that the pressure inside the input chamber 24 is set at the set positive pressure value P1set (e.g., 180 mmHg).

2. When the balloon pump 33 is sufficiently expanded, that is, when the plate 27 reaches the predetermined position STset1 during the expansion period, the solenoid valve 50 is closed to hold the balloon pump 33 in the expanded state until the subsequent contraction of the pump 33 begins.

With the solenoid valves 14 and 44 closed and opened, respectively, the pressure inside the input chamber 24 is set in advance at the pressure value V2set (e.g., −150 mmHg) required at the beginning of the subsequent contraction period.

At the same time, the pressure inside the positive pressure tank 12 the supply of which has already been cut off by means of the solenoid valve 14 is set in advance at the pressure value P2set required at the beginning of the subsequent expansion period.

(ii) Contraction period of the balloon pump 33:

1. Before the contraction period begins, the solenoid valve 50 is closed and the balloon pump 33 is therefore held in the expanded state. At this time, the solenoid valves 14 and 44 are in the closed and open positions, respectively. Accordingly, the pressure inside the input chamber 24 is set at the set negative pressure value V2set (e.g., −150 mmHg) for the internal pressure of the positive pressure tank 42, the value V2set being set by means of the solenoid valve 41. When, in this state, the solenoid valve 50 is opened, the plate 27 is moved in a direction in which the balloon pump 33 is contracted. At this time, in order to prevent application of an excessively high pressure to the inside of the balloon pump 33, the internal pressure of the negative pressure tank 42 is adjusted so that the pressure inside the input chamber 24 is set at the set negative pressure value V1set (e.g., −20 mmHg).

2. When the balloon pump 33 is sufficiently contracted, that is, when the plate 27 reaches the predetermined position STset0 during the contraction period, the solenoid valve 50 is closed to hold the balloon pump 33 in the contracted state until the subsequent expansion of the pump 33 begins.

With the solenoid valves 14 and 44 opened and closed, respectively, the pressure inside the input chamber 24 is set in advance at the pressure value P2set (e.g., 300 mmHg) required at the beginning of the subsequent expansion period.

At the same time, the pressure inside the negative pressure tank 42 the supply of which has already been cut off by means of the solenoid valve 44 is set in advance at the pressure value V2set required at the beginning of the subsequent contraction period.

It should be noted that the relationship between the various set values is as follows. (Set positive pressure values)

$0 < P1set < P2set$ (Set negative pressure values)

$V2set < V1set < 0$

As has been described above, it is possible, according to the present invention, to allow the input chamber of the isolator means to communicate with the negative pressure source while maintaining the medical appliance in the expanded state. Therefore, when the medical appliance is supplied with a negative pressure during the subsequent contraction period by opening the valve means, the input chamber of the isolator means has already been supplied with the required negative pressure. Accordingly, it is possible to eliminate the effect of resistance generated in the pipe line extending from the negative pressure source to the isolator means, and the input chamber of the isolator means can be pressurized in advance, so that it is possible to quickly switch the state of the medical appliance from expansion to contraction.

During the contraction period of the medical appliance, the input chamber of the isolator means can be communicated with the positive pressure source while the medical appliance is held in the contracted state. Therefore, when the medical appliance is supplied with a positive pressure in the subsequent expansion period by opening the valve means, the input chamber of the isolator means has already been supplied with the required positive pressure. Accordingly, it is possible to eliminate the effect of resistance generated in the pipe line which extends from the positive pressure source to the isolator means, and the input chamber of the isolator means can be pressurized in advance, so that it is possible to quickly switch the state of the medical appliance from contraction to expansion.

Although the present invention has been described through specific terms, it should be noted here that the described embodiment is not necessarily limitative and various changes and modifications may be imparted thereto without departing from the scope of the invention which is limited solely by the appended claims.

What is claimed is:

1. A medical appliance driving apparatus comprising:
   positive pressure supply means for supplying a positive pressure;
   negative pressure supply means for supplying a negative pressure;
   switching valve means connected to both said positive and negative pressure supply means to alternately output positive and negative pressures upon operation of said switching valve means;
   isolator means having an input chamber and an output chamber which are defined by a movable membrane, said input chamber being connected to said switching valve means;
   output valve means having an input side connected to said output chamber of said isolator means and an output side;
   a medical appliance connected to the output side of said output valve means; and
   electronic control means for controlling said output valve means and for controlling said switching valve means alternately connect the input chamber of said isolator means to the positive pressure supply means and the negative pressure supply means only when said output valve means is closed.

2. An apparatus according to claim 1, wherein said electronic control means switches said switching valve means to the positive pressure side and opens said output valve means to supply a positive pressure to said medical appliance, and then closes said output valve means to maintain the pressure supplied to said medical appliance and switches said switching valve means to the negative pressure side to supply a negative pressure to said input chamber of said isolator means.

3. An apparatus according to claim 2, wherein said electronic control means switches said switching valve means to the negative pressure side and opens said output valve means to supply a negative pressure to said medical appliance, and then closes said output valve means to maintain the pressure supplied to said medical appliance and switches said switching valve means to the positive pressure side to supply a positive pressure to said input chamber of said isolator means.

4. An apparatus according to claim 3, wherein said electronic control means effects control so that a positive or negative pressure which is supplied to said input chamber of said isolator means while the pressure which has previously been supplied to said medical appliance is being maintained is adjusted so as to be higher or lower than a respective set positive or negative pressure which is to be supplied to said input chamber of said isolator means in a state wherein said output valve means is open.

5. An apparatus according to claim 1, further comprising:
   position detecting means for detecting the position of said movable membrane of said isolator means,
   wherein said electronic control means closes said output valve means when said movable membrane has moved to a first predetermined position in a state wherein said input chamber of said isolator means is communicated with said positive pressure supply means by the action of said switching valve means and said output valve means is open, and further activates said switching valve means to allow said input chamber of said isolator means to communicate with said negative pressure supply means.

6. An apparatus according to claim 5, wherein said electronic control means closes said output valve means when said movable membrane has moved to a second predetermined position in a state wherein said input chamber of said isolator means is communicated with said negative pressure supply means by the action of said switching valve means and said output valve means is in its open position, and further activtes said switching valve means to allow said input chamber of said isolator means to communicate with said positive pressure supply means.

7. An apparatus according to claim 6, wherein said positive pressure supply means has first pressure detecting means for detecting a positive pressure supplied from said positive pressure supply means, and said electronic control means effects control, in a state wherein said input chamber of said isolator means is communicated with said positive pressure supply means, so that, in a state wherein said output valve means is closed, the pressure supplied from said positive pressure supply means is adjusted to a first set positive pressure value (P2set), whereas, in a state wherein said output valve means is open, the pressure supplied from said positive pressure supply means is adjusted to a second set positive pressure value (P1set).

8. An apparatus according to claim 7, wherein said negative pressure supply means has second pressure detecting means for detecting a negative pressure supplied from said negative pressure supply means, and said electronic control means effects control, in a state wherein said input chamber of said isolator means is communicated with said negative pressure supply means, so that, in a state wherein said output valve means is closed, the pressure supplied from said negative pressure supply means is adjusted to a first set negative pressure value (V2set), whereas, in a state wherein said valve means is open, the pressure supplied from said negative pressure supply means is adjusted to a second set negative pressure value (V1set).

9. An apparatus according to claim 8, wherein said positive pressure supply means includes a compressor, a pressure regulating valve and a positive pressure tank, said first pressure detecting means being adapted to detect the pressure in said positive pressure tank, said electronic control means further effecting control such that the pressure in said positive pressure tank is adjusted to said first set positive pressure value (P2set) when said input chamber of said isolator means is in communication with said negative pressure supply means side through said switching valve means.

10. An apparatus according to claim 9, wherein said negative pressure supply means includes a vacuum pump, a pressure regulating valve and a negative pressure tank, said second pressure detecting means being adapted to detect the pressure in said negative pressure tank, said electronic control means further effecting control such that the pressure in said negative pressure tank is adjusted to said first set negative pressure value (V2set) when said input chamber of said isolator means is in communication with said positive pressure supply means side through said switching valve means.

11. An apparatus according to claim 1, wherein said medical appliance is a balloon pump.

12. An apparatus according to claim 1, further comprising means for supplying and discharging helium gas, said means being connected between said output chamber of said isolator means and the input side of said output valve means.

* * * * *